United States Patent
Kim et al.

(10) Patent No.: US 11,613,427 B2
(45) Date of Patent: Mar. 28, 2023

(54) HORIZONTAL-FLOW-TYPE APPARATUS FOR AUTOMATICALLY TRANSPORTING REAGENT CARTRIDGES

(71) Applicant: BODITECH MED INC., Gangwon-do (KR)

(72) Inventors: Byeong Chul Kim, Gangwon-do (KR); Young Haeng Lee, Seoul (KR); Kyong Hwa Chong, Gyeonggi-do (KR); Min Hwan Lee, Seoul (KR); Yu Jin Park, Gangwon-do (KR)

(73) Assignee: BODITECH MED INC., Gangwon-Do (KR)

( * ) Notice: Subject to any disclaimer, the term of this patent is extended or adjusted under 35 U.S.C. 154(b) by 410 days.

(21) Appl. No.: 15/768,759

(22) PCT Filed: Oct. 28, 2016

(86) PCT No.: PCT/KR2016/012254
§ 371 (c)(1),
(2) Date: Apr. 16, 2018

(87) PCT Pub. No.: WO2017/074102
PCT Pub. Date: May 4, 2017

(65) Prior Publication Data
US 2018/0305135 A1    Oct. 25, 2018

(30) Foreign Application Priority Data

Oct. 28, 2015    (KR) .................. 10-2015-0150342

(51) Int. Cl.
*B65G 47/06*        (2006.01)
*B65G 47/26*        (2006.01)
(Continued)

(52) U.S. Cl.
CPC ............. *B65G 47/06* (2013.01); *B65G 47/26* (2013.01); *B65G 47/268* (2013.01); *B65G 47/82* (2013.01);
(Continued)

(58) Field of Classification Search
None
See application file for complete search history.

(56) References Cited

U.S. PATENT DOCUMENTS 3,053,581 A * 9/1962 Werner ...................... B60J 7/02
16/93 R
3,533,744 A * 10/1970 Unger ..................... G01N 35/02
436/63

(Continued)

FOREIGN PATENT DOCUMENTS

| CN | 202210102 U | 5/2012 |
| CN | 203759025 U | 8/2014 |

(Continued)

OTHER PUBLICATIONS

International Search Report issued by ISA/KR in connection with PCT/KR2016/012254 dated Feb. 21, 2017.
(Continued)

*Primary Examiner* — Benjamin R Whatley
*Assistant Examiner* — Curtis A Thompson
(74) *Attorney, Agent, or Firm* — Levenfeld Pearlstein, LLC

(57) ABSTRACT

The present invention relates to a horizontal-flow-type apparatus for automatically transporting reagent cartridges. The apparatus includes: a magazine (110) in which a plurality of reagent cartridges (1) is stacked; a conveyer belt (120) having a plurality of separating projections (121) arranged in a conveying direction to horizontally separately convey the reagent cartridges (1); a driving motor (130) for driving the
(Continued)

conveyer belt (120); a feeding unit (140) for feeding the reagent cartridges (1) stacked in the magazine (110) onto the conveyer belt (120); an examining unit (150) disposed over the front end of the conveyer belt (120) to examine the reagent cartridges (1); and reagent cartridge aligning members (161, 162) disposed in the conveying line of the conveyer belt (120), opposite to the examining unit (150), to align the reagent cartridges (1) in position.

3 Claims, 4 Drawing Sheets

(51) Int. Cl.
| | | |
|---|---|---|
| *B65G 47/82* | (2006.01) | |
| *G01N 21/25* | (2006.01) | |
| *G01N 35/04* | (2006.01) | |
| *G01N 21/17* | (2006.01) | |
| *G01N 35/02* | (2006.01) | |
| *G01N 1/10* | (2006.01) | |
| *G01N 1/18* | (2006.01) | |
| *G16H 10/40* | (2018.01) | |
| *G01N 35/00* | (2006.01) | |
| *G01N 35/10* | (2006.01) | |

(52) U.S. Cl.
CPC ........... *G01N 21/17* (2013.01); *G01N 21/251* (2013.01); *G01N 35/021* (2013.01); *G01N 35/04* (2013.01); *G01N 1/10* (2013.01); *G01N 1/18* (2013.01); *G01N 35/00029* (2013.01); *G01N 35/00732* (2013.01); *G01N 35/1002* (2013.01); *G01N 2035/00089* (2013.01); *G01N 2035/00108* (2013.01); *G01N 2035/0425* (2013.01); *G01N 2035/0465* (2013.01); *G16H 10/40* (2018.01)

(56) References Cited

U.S. PATENT DOCUMENTS

| | | | | |
|---|---|---|---|---|
| 3,939,634 | A * | 2/1976 | Yoshizawa | B65H 67/067 242/473.6 |
| 4,855,109 | A * | 8/1989 | Muraishi | G01N 35/00029 422/63 |
| 4,960,566 | A * | 10/1990 | Mochida | B01L 9/065 422/503 |
| 5,356,595 | A * | 10/1994 | Kanamori | G01N 1/2813 118/100 |
| 5,578,268 | A * | 11/1996 | Champseix | B01F 9/002 422/63 |
| 2002/0031844 | A1* | 3/2002 | Komatsu | G01N 35/00029 436/518 |
| 2002/0062111 | A1* | 5/2002 | Itoh | G01N 35/00594 604/318 |
| 2004/0191925 | A1* | 9/2004 | Seto | G01N 35/00029 436/514 |
| 2007/0264157 | A1* | 11/2007 | Takagi | G01N 33/493 422/64 |
| 2008/0267446 | A1* | 10/2008 | Capewell | G01N 21/8483 382/100 |
| 2010/0303590 | A1* | 12/2010 | Pedrazzini | G01N 35/04 414/331.02 |
| 2012/0046203 | A1* | 2/2012 | Walsh | B01L 3/502761 422/69 |
| 2012/0269682 | A1* | 10/2012 | Watanabe | G01N 35/00663 422/68.1 |
| 2014/0090957 | A1* | 4/2014 | Yamauchi | B65G 47/52 198/418.5 |

FOREIGN PATENT DOCUMENTS

| | | | | |
|---|---|---|---|---|
| EP | 0260136 | A2 | 3/1988 | |
| JP | H04345418 | A * | 12/1992 | ............ B65G 21/20 |
| JP | H04345418 | A | 12/1992 | |
| JP | 201006537 | * | 3/2010 | ............ G01N 35/04 |
| KR | 100450519 | B1 | 10/2004 | |
| KR | 100747148 | B1 | 8/2007 | |
| KR | 1020130029127 | A | 3/2013 | |
| WO | 0221144 | A1 | 3/2002 | |
| WO | 2005006831 | A2 | 1/2005 | |

OTHER PUBLICATIONS

Extended European Search Report issued by EPO in connection with EP16860285 dated Jun. 13, 2019.

* cited by examiner

HORIZONTAL-FLOW-TYPE APPARATUS FOR AUTOMATICALLY TRANSPORTING REAGENT CARTRIDGES

TECHNICAL FIELD

The present invention relates to a horizontal-flow-type apparatus for automatically transporting reagent cartridges.

BACKGROUND ART

Most equipment for clinical immunoassays use blood collection tubes for keeping blood taken from patients at a hospital. Most of the equipment separate plasmas and corpuscles from blood in blood collection tubes through centrifugal separation and keep only the plasmas for examination.

Various analysis techniques such as enzyme assay, immunoassay, chemical colorimetric assay, electrochemical assay, fluorescence labeling and measuring, and chemiluminescent labeling and measuring have been used in the field of medical diagnosis to detect or quantify specific samples contained in biological samples such as blood, a serum, urine, and cell sap.

Those analysis techniques have been applied to large equipment such as automatic analysis apparatuses that are used at a clinical trial center of a large hospital, or POCT (Point of Care Testing) equipment using platforms such as test strips or cartridges.

Large equipment has the advantage of being able to handle a large amount of samples and having high reliability in the measured values, but the structures are complicated and large due to the characteristics of the mechanical configuration, so they are used only in specific laboratories and have a spatial limit. Further, the equipment requires preprocessing of biological samples and it is required to periodically replace various reagents and sensors, so users have difficulty in terms of maintenance.

However, POCT equipment, as compared with large equipment, is lower in reliability of measured values, but has no limit in measurement place and can enable performing quick measurements, so it is widely used in the field of medical diagnosis.

At present, about 90% of examinations are performed at a central laboratory, but products and equipment for POCT are increasingly used because they can provide quick examination results, reduce costs, and improve the diagnostic quality.

Further, the accuracy of POCT equipment has increased up to the level of large clinical diagnostic equipment with development of field examinations, thus the POCT market is increasing. Accordingly, the demands for POCT equipment are increasing and POCT equipment is being developed for examining more people.

When examining a lot of people, the technician feels much fatigue and the possibility of errors in the examination results are accordingly increased, so it is increasingly required to develop an automatic examination system that can handle a large amount of reagents to reduce fatigue of the technician using the system. A cartridge type automation system is limited in size by the size of cartridges and the measurement direction, so the present invention has been made to provide an automatic conveying system that can automatically perform preprocessing of cartridges.

DOCUMENTS OF RELATED ART

Korean Patent Application Publication No. 10-2013-0029127 (published on Mar. 21, 2013)

DISCLOSURE

Technical Problem

The present invention has been made in an effort to solve the problems in the related art and an object of the present invention is to provide an apparatus for automatically transporting reagent cartridges, the apparatus being able to automatically convey a large amount of reagent cartridges to an examination position in a small space.

Technical Solution

An apparatus for automatically transporting reagent cartridges of the present invention includes: a magazine in which a plurality of reagent cartridges is stacked; a conveyer belt having a plurality of separating projections arranged in a conveying direction to horizontally separately convey the reagent cartridges; a driving motor for driving the conveyer belt; a feeding unit for feeding the reagent cartridges stacked in the magazine onto the conveyer belt; and an examining unit disposed over a front end of the conveyer belt to examine the reagent cartridges.

The apparatus may further include reagent cartridge aligning members disposed in a conveying line of the conveyer belt, opposite to the examining unit, to align the reagent cartridges in position.

The reagent cartridge aligning members may include a first elastic member laterally elastically supporting the reagent cartridges with respect to the conveying direction and second elastic members vertically elastically supporting the reagent cartridges with respect to the conveying direction. The first elastic member or the second elastic members may be plate springs.

The feeding unit may include: a cartridge loader disposed under the magazine to be able to move forward and backward; and an actuator for moving the cartridge loader forward and backward.

Advantageous Effects

Since the apparatus for automatically transporting reagent cartridges of the present invention includes the magazine in which reagent cartridges are stacked and the conveyer belt for horizontally conveying the reagent cartridges stacked in the magazine to the examining unit, it is possible to convey a large amount of reagent cartridges in a small space, so the equipment can be reduced in size. Further, since the apparatus includes the conveyer belt as a conveying unit, it is possible to freely design the conveying distance in consideration of the amount of reagent to be handled, and to simplify the operation mechanism.

Further, since the apparatus includes the reagent cartridge aligning members that can align the reagent cartridges the examination position, it is possible to achieve high examination accuracy without an error.

BEST MODE

Specific structures and functions stated in the following embodiments of the present invention are exemplified to illustrate embodiments according to the spirit of the present invention and the embodiments according to the spirit of the present invention can be achieved in various ways. Further, the present invention should not be construed as being limited to the following embodiments and should be construed as including all changes, equivalents, and replacements included in the spirit and scope of the present invention.

Further, in the specification, terms including "first" and/or "second" may be used to describe various components, but the components are not limited to the terms. The terms are used to distinguish one component from another component, and for instance, a first component may be referred to as a second component, and similarly, a second component may be referred to as a first component without departing from the scope according to the spirit of the present invention.

It should be understood that when one element is referred to as being "connected to" or "coupled to" another element, it may be connected directly to or coupled directly to another element or be connected to or coupled to another element, having the other element intervening therebetween. On the other hand, it is to be understood that when one element is referred to as being "connected directly to" or "in contact directly with" another element, it may be connected to or coupled to another element without the other element intervening therebetween. Expressions for describing relationships between components, that is, "between", "directly between", "adjacent to", and "directly adjacent to" should be construed in the same way.

Terms used in the present specification are used only in order to describe specific exemplary embodiments rather than limiting the present invention. As used herein, the singular forms are intended to include the plural forms as well, unless the context clearly indicates otherwise. It will be further understood that the terms "comprises" or "have" used in this specification, specify the presence of stated features, steps, operations, components, parts, or a combination thereof, but do not preclude the presence or addition of one or more other features, numerals, steps, operations, components, parts, or a combination thereof.

Hereinafter, the present invention will be described in detail with reference to the accompanying drawings.

Figure 1:
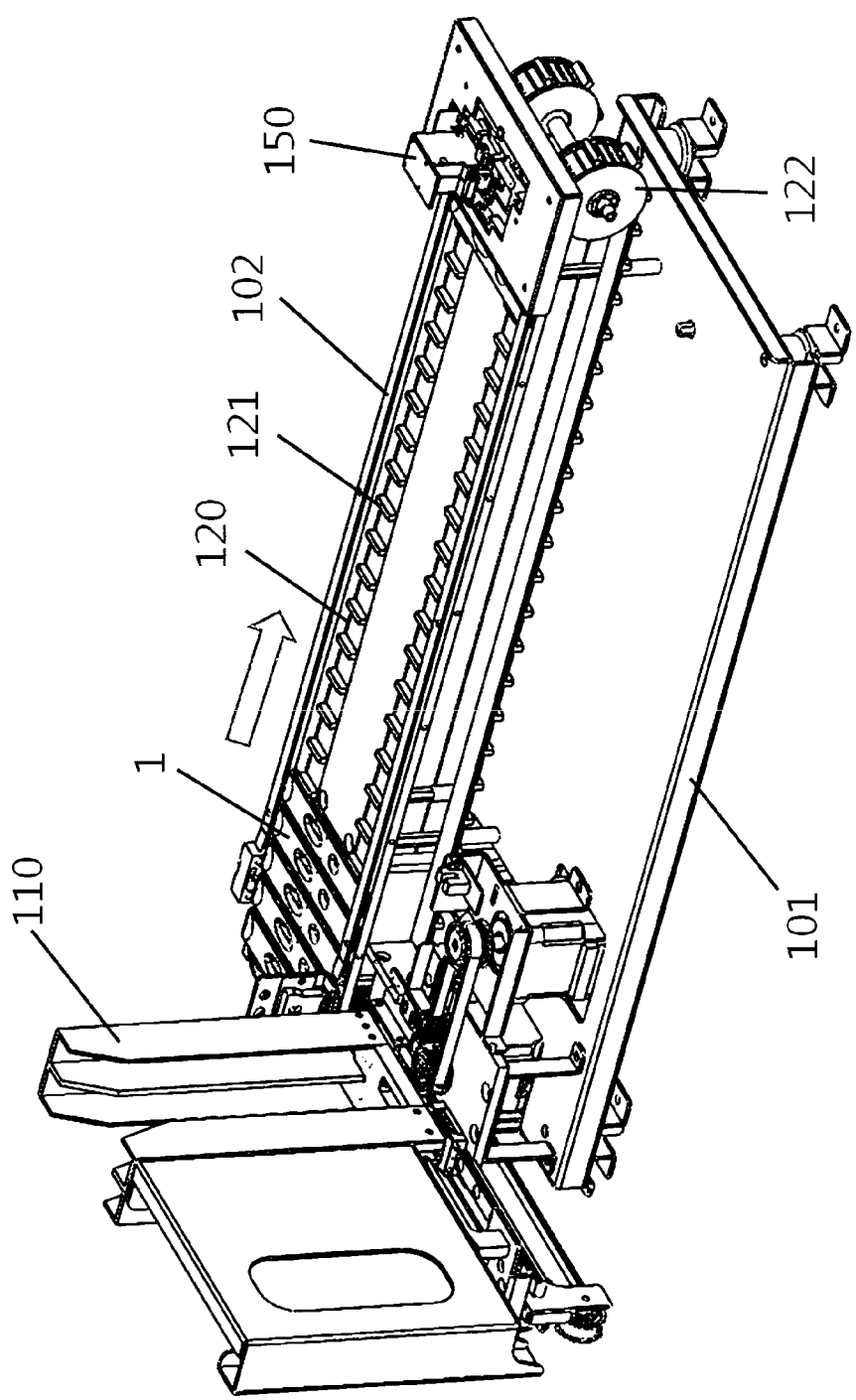
FIG. 1 is a view showing the entire configuration of an apparatus for automatically transporting reagent cartridges according to the present invention.

Referring to FIG. 1, an apparatus for automatically transporting reagent cartridges of the present invention (referred to as a 'conveying apparatus' in abbreviation) includes: a magazine 110 in which a plurality of reagent cartridges 1 is stacked; a conveyer belt 120 having a plurality of separating projections 121 arranged in a conveying direction to horizontally convey the reagent cartridges 1; a driving motor for driving the conveyer belt 120; a feeding unit 140 for feeding the reagent cartridges 1 stacked in the magazine 110 onto the conveyer belt 120; an examining unit 150 disposed over the front end of the conveyer belt 120 to examine the reagent cartridges 1; and reagent cartridge aligning members disposed in the conveying line of the conveyer belt 120, opposite to the examining unit 150, to align the reagent cartridges 1 in position.

The conveyer belt 120 is horizontally disposed on a base plate 101 and has the separating projections 121 vertically protruding and arranged in the conveying direction, and the reagent cartridges 1 are positioned between the separating projections 121 and conveyed. The separating projections 121 keep the reagent cartridges in their positions while the reagent cartridges are conveyed on the conveyer belt 120 to the examination position.

Guide rails 102 are disposed at both sides of the conveyer belt 120 to prevent the reagent cartridges 1 from being laterally dropped while they are conveyed.

The magazine 110 is disposed at a first end of the conveyer belt 120 and the examining unit 150 is disposed at a second end of the conveyer belt 120, so the reagent cartridges 1 stacked in the magazine 110 are horizontally conveyed on the conveyer belt 120 to the examining unit 150.

Idle rollers 122 for supporting load are disposed at the first end of the conveyer belt 120 and a driving motor is disposed at the second end, whereby the conveyer belt 120 is rotated. The driving motor may be a stepping motor that can accurately control a rotational angle to be able to accurately control the conveying position of the reagent cartridge.

The reagent cartridges 1 conveyed on the conveyer belt 120 and examined by the examining unit 150 are turned by the idle rollers 122 and discharged outside the conveying apparatus by rotation of the conveyer belt 120.

The feeding unit is disposed under the magazine 110 to feed the reagent cartridges stacked in the magazine 110 onto the conveyer belt 120. The feeding unit horizontally pushes the lowermost reagent cartridge of the reagent cartridges stacked in the magazine 110 to the conveyer belt 120.

Figure 2:
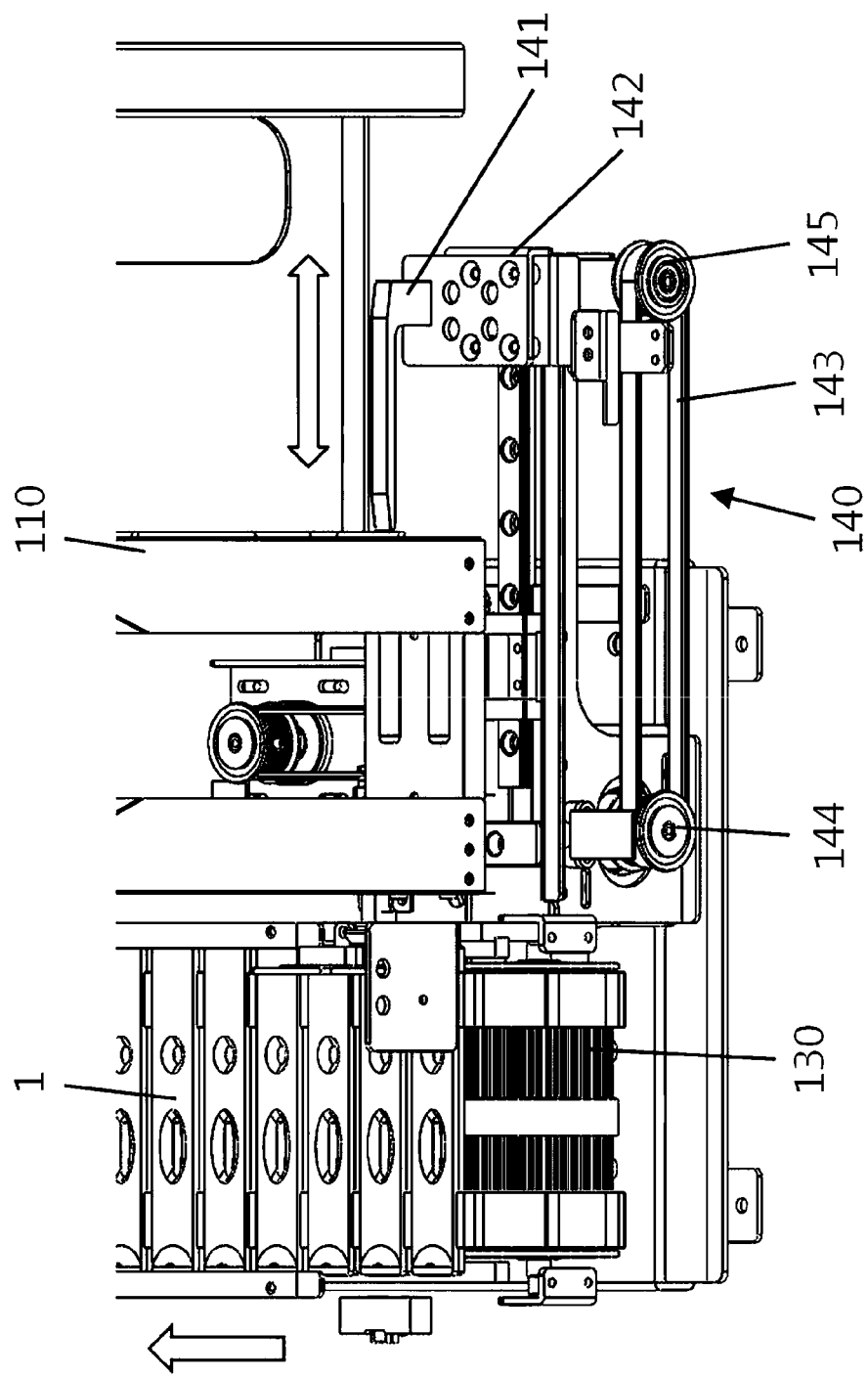
FIG. 2 is a view showing the main parts of a feeding unit in the apparatus for automatically transporting reagent cartridges according to the present invention.

FIG. 2 is a view showing the main parts of the feeding unit in the apparatus for automatically transporting reagent cartridges according to the present invention.

In detail, the feeding unit 140 includes a cartridge loader 141 that can move forward and backward and an actuator for moving the cartridge loader 141 forward and backward. The actuator in this embodiment includes a belt 143 supported and rotated by a driving wheel 144 and an idle wheel 145 and a fixed block 142 integrally formed with the cartridge loader 141 and fixed to the belt 143.

According to the feeding unit 140, when the driving wheel 144 is rotated forward and backward, the belt 143 is rotated forward and backward and the cartridge loader 141 fixed to the belt 143 is moved forward and backward.

Although the cartridge loader is a belt type moving forward and backward in this embodiment, the present invention is not limited thereto and other well-known device such as a linear motor may be used.

Reference numeral '130' indicates the driving motor for driving the conveyer belt.

The driving motor 130 for driving the conveyer belt and the driving wheel 144 moving the cartridge loader 141 forward and backward are controlled by a specific controller. The controller can appropriately synchronize the operation speeds of the driving motor 130 and the cartridge loader 141, so the reagent cartridges 1 discharged out of the magazine 110 can be accurately positioned between the separating projections of the conveyer belt.

Figure 3A:
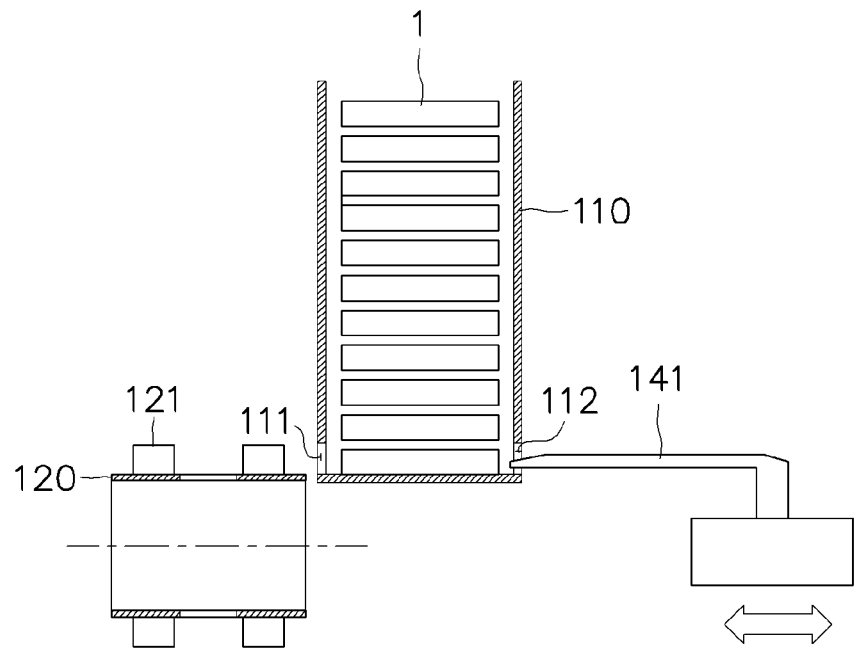
FIGS. 3A and 3B are views showing exemplary operation of the feeding unit in the apparatus for automatically transporting reagent cartridges according to the present invention.
Figure 3B:
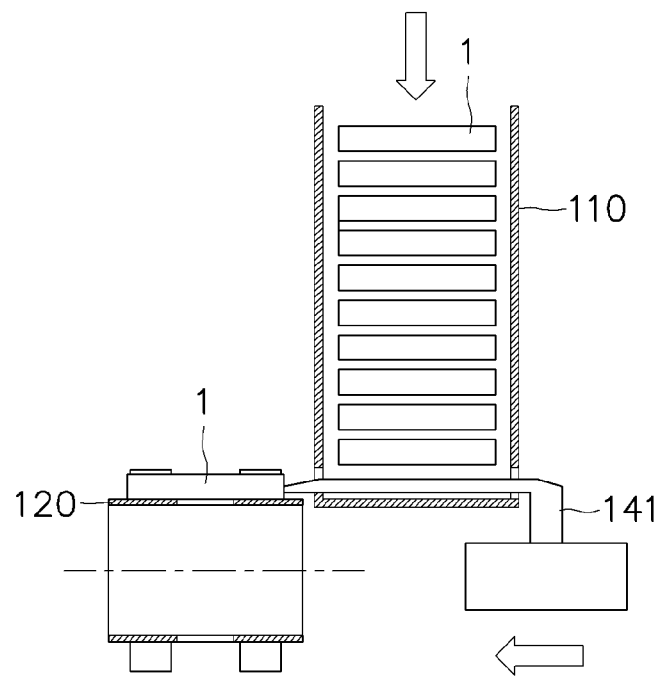

FIGS. 3A and 3B are views showing exemplary operation of the inlet unit in the apparatus for automatically transporting reagent cartridges according to the present invention.

Referring to FIG. 3A, the magazine 110 has an outlet 111 at the lower end and an inlet 112 opposite to the outlet 111 so that the front end of the cartridge loader 141 can be inserted through the inlet 112.

The reagent cartridges 1 are stacked in the magazine 110.

As shown in FIG. 3B, the cartridge loader 141 moves forward and pushes a reagent cartridge 1 in the magazine 1 onto the conveyer belt 120. When the lowermost reagent cartridge 1 is discharged out of the magazine 110, the stacked reagent cartridges 1 are moved down by the weight and the cartridge loader 141 moves back and then moved forward, thereby pushing the next reagent cartridge 1 onto the conveyer belt 120.

Referring to FIG. 1 again, the reagent cartridges 1 pushed on the conveyer belt 120 from the magazine 110 are horizontally moved on the conveyer belt 120 to the examining unit 150, and preprocessing may be performed, if necessary, while the reagent cartridges are conveyed to the examining unit 150.

The reagent cartridges 1 are examined at the examining unit 150.

In particular, the reagent cartridge aligning members are provided so that the reagent cartridges 1 can be aligned and examined at a predetermined position by the examining unit 150.

Figure 4A:
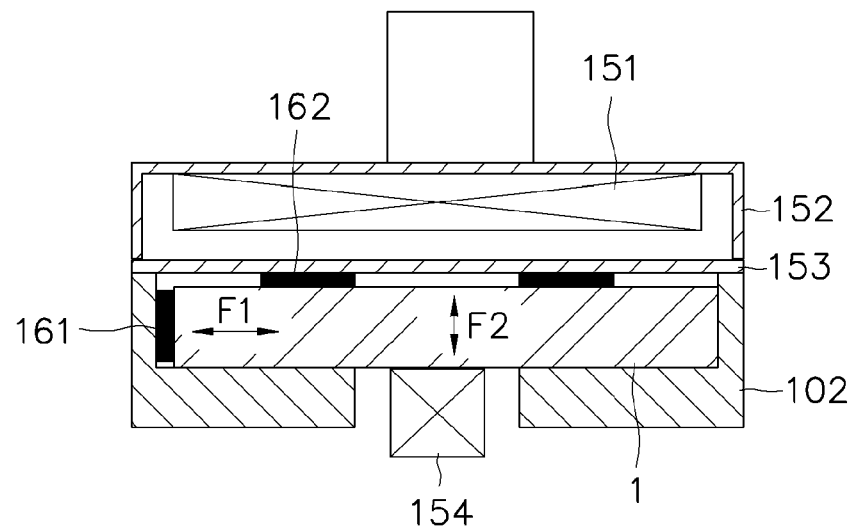
FIGS. 4A and 4B are views showing an example of reagent cartridge aligning members in the apparatus for automatically transporting reagent cartridges according to the present invention.
Figure 4B:
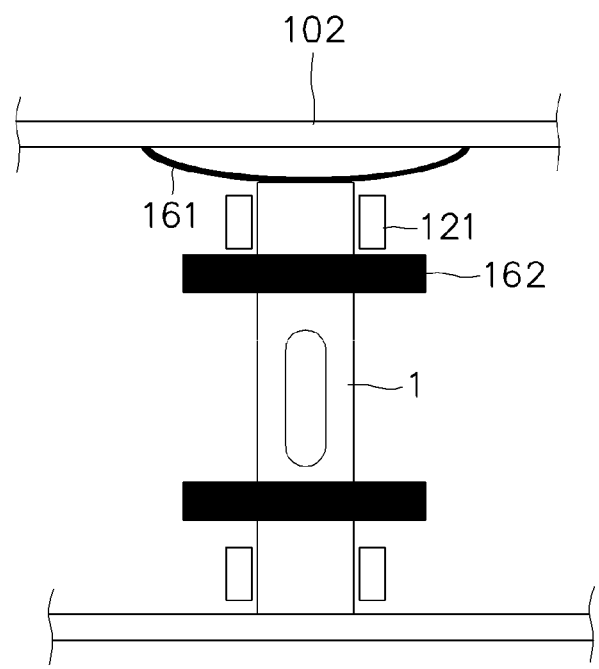

FIGS. 4A and 4B are views showing an example of reagent cartridge aligning members in the apparatus for automatically transporting reagent cartridges according to the present invention. FIG. 4A is a vertical cross-sectional view and FIG. 4B is a plan view without the examining unit.

Referring to FIGS. 4A and 4B, the examining unit in this embodiment includes an optical unit 151, a top fixing plate 152 fixing the top of the optical unit 151, and a bottom fixing plate 153 fixing the bottom of the optical unit 151. The reagent cartridge aligning members 161 and 162 are disposed in the conveying line under the optical unit 151.

In detail, the reagent cartridge aligning members 161 and 162 include a first elastic member 161 laterally elastically supporting the reagent cartridges 1 with respect to the conveying direction and second elastic members 162 vertically elastically supporting the reagent cartridges 1 with respect to the conveying direction.

The first elastic member 161 may be fixed to the guide rails 102 to elastically support a side of a reagent cartridge 1 and the second elastic members 162 may be fixed to the bottom fixing plate 153 to elastically support the top of a reagent cartridge 1. The first and second elastic members may be plate springs, that is, single plate springs or multi-plate springs.

In the reagent cartridge aligning members 161 and 162, the first elastic member 161 horizontally elastically support a reagent cartridge 1 (in the direction F1) to horizontally hold the reagent cartridge in position and the second elastic members 162 vertically elastically support the reagent cartridge 1 (in the direction F2) to vertically hold the reagent cartridge in position.

That is, when the reagent cartridge 1 is conveyed under the examining unit, it can be aligned at the predetermined position for examination by the reagent cartridge aligning members 161 and 162 and then examined, so accurate examination can be performed without an error.

Reference numeral '154' indicates a detection switch for detecting a reagent cartridge positioned at the examination position and the detection switch may be a proximity sensor of a photo sensor.

The present invention is not limited to the embodiment described above and the accompanying drawings and may be changed and modified in various ways without departing from the scope of the present invention by those skilled in the art.

| [Description of Reference Numerals] | |
|---|---|
| 1: Reagent cartridge | 110: Magazine |
| 120: Conveyer belt | 121: Separating projection |
| 130: Driving motor | 140: Feeding unit |
| 150: Examining unit | 161: First elastic member |
| 162: Second elastic member | |

The invention claimed is:

1. An apparatus for automatically transporting reagent cartridges, the apparatus comprising:
   a magazine in which a plurality of reagent cartridges is stacked;
   a conveyer belt having a plurality of separating projections arranged in a conveying direction to convey the reagent cartridges, wherein each of the reagent cartridges is arranged on a surface of the conveyer belt between the separating projections.
   a guide rail disposed at a side of the conveyer belt to prevent the reagent cartridges from being laterally dropped;
   a fixing plate disposed at a top of the conveyer belt;
   a driving motor for driving the conveyer belt;
   a feeding unit for feeding the reagent cartridges stacked in the magazine onto the conveyer belt, the feeding unit including a cartridge loader configured to move the reagent cartridges onto the conveyer belt one at a time;
   an examining unit disposed over a front end of the conveyer belt to examine the reagent cartridges; and
   an aligning member for aligning the reagent cartridges in an examining position over the conveyor belt with respect to the examining unit,
   wherein the aligning member comprises a first elastic member separately supporting a reagent cartridge with respect to the guide rail in a horizontal direction, and a second elastic member separately supporting a top of the reagent cartridge with respect to the examining unit in a vertical direction, and wherein the second elastic member comprises a middle portion in contact with the top of the reagent cartridge and outer edges directly connected to the fixing plate for aligning the reagent cartridge.

2. The apparatus of claim 1, wherein the first elastic member or the second elastic member is a plate spring.

3. The apparatus of claim 1, wherein the cartridge loader is disposed under the magazine to be able to move forward and backward; and wherein the feeding unit further includes an actuator for moving the cartridge loader forward and backward.

* * * * *